US006168949B1

(12) United States Patent
Rubenberger

(10) Patent No.: US 6,168,949 B1
(45) Date of Patent: Jan. 2, 2001

(54) BIOREACTOR WITH VORTEX MIXING CHAMBER

(76) Inventor: Karl Rubenberger, Dall'Armi-Strasse 5, Erding (DE), 85435

( * ) Notice: Under 35 U.S.C. 154(b), the term of this patent shall be extended for 0 days.

(21) Appl. No.: 08/772,279

(22) Filed: Dec. 20, 1996

(30) Foreign Application Priority Data

Dec. 21, 1995 (DE) ............................................. 295 20 294

(51) Int. Cl.[7] ............................... C12M 1/04; C12M 1/02
(52) U.S. Cl. ......................... 435/295.1; 435/261; 435/818
(58) Field of Search .............................. 435/283.1, 286.6, 435/287.8, 295.1, 261, 818

(56) References Cited

U.S. PATENT DOCUMENTS

| | | | | |
|---|---|---|---|---|
| 1,517,598 | * | 12/1924 | Stevenson | 239/404 |
| 3,957,585 | * | 5/1976 | Malick | 435/246 |
| 4,244,815 | * | 1/1981 | Chaikin et al. | 210/622 |
| 4,260,110 | * | 4/1981 | Werding | 239/404 |
| 4,957,626 | * | 9/1990 | Ashbrook et al. | 210/695 |
| 5,059,357 | * | 10/1991 | Wolf et al. | 261/53 |
| 5,166,067 | * | 11/1992 | Ishida et al. | 435/401 |
| 5,549,917 | * | 8/1996 | Cherukuri et al. | 426/96 |

FOREIGN PATENT DOCUMENTS

95/16521 6/1995 (WO) .

* cited by examiner

*Primary Examiner*—John P. Weber
*Assistant Examiner*—Patricia Patten
(74) *Attorney, Agent, or Firm*—Jacobson, Price, Holman & Stern, PLLC

(57) ABSTRACT

The invention relates to an apparatus for the aerobic multiplication of micro-organisms. A tank with a conical bottom shape holds the fermentation broth and a circulating pump outside the tank circulates the fermentation broth from the bottom of the tank to the top. A heat exchanger maintains the desired process temperature. In accordance with the invention, the apparatus includes at least one atomizing nozzle contained within a vortex chamber for the fine atomization of the fermentation broth and for the mixing with process gas in the top of the tank above the fermentation broth. The fermentation broth in the lower portion of the tank is at a quiescent state without mechanical agitation.

15 Claims, 2 Drawing Sheets

BIOREACTOR WITH VORTEX MIXING CHAMBER

Figure 1:
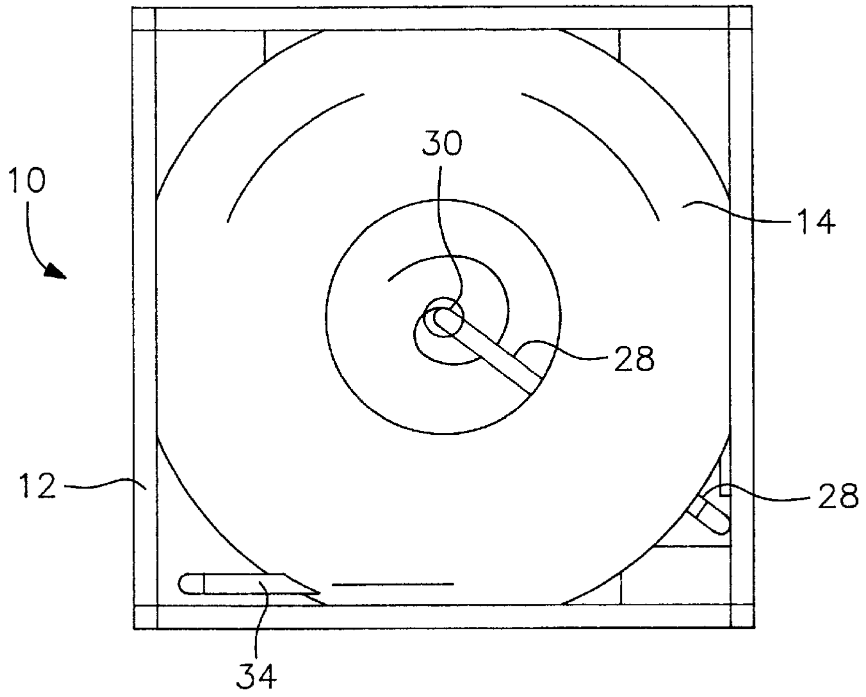

The present invention relates to an apparatus for the aerobic multiplication of micro-organisms including a tank for the acceptance of a fermentation broth and a heat exchanger for setting a desired process temperature.

Such apparatus, which are also called fermenters, are already largely well known. In these, the so-called submerged process is used in which the cells are developed within the fluid. The fermenters used in the prior art are as a rule cylindrical steel or stainless steel tanks. Cooling is performed using a double jacket, by means of tank coils or other installations. In the tank, an agitator serves the powerful mixing of the fluid. The process gas, which usually consists of air, is blown into the fermentation broth through a strainer in bubbles which are as small as possible. In aerobic processes a sufficient supply of oxygen is of decisive importance by means of a supply of sterilised air or of pure oxygen. This is where the disadvantages of conventional fermenters for the performance of the submerged process can be found. Due to the non-uniform distribution of bubble sizes in the process gas introduced and to an insufficient mixing, the oxygen supply is frequently not sufficient so that the multiplication of the micro-organisms is not performed optimally.

The object of the present invention is to ensure a sufficient process gas supply during fermentation.

This object is solved in accordance with the invention on the basis of an apparatus of the generic type by at least one atomising nozzle provided for the fine atomisation of the fermentation broth and for the mixture with the process gas.

In accordance with a preferred embodiment of the invention, the tank for the acceptance of the fermentation broth has a conical shape in the part extending to the bottom. In the lower area of the cone, a lead begins which leads to a circulating pump. From the circulating pump a lead is then provided into the upper area of the tank with at least one atomising nozzle being positioned on that area of the lead which protrudes into the tank. The fermenter is filled with the fermentation broth in the lower area and the upper area contains the process gas atmosphere, that is, for example, air. The pump-circulated fermentation broth is mixed intensively with the process gas via the atomising nozzle. In this way, the process gas is brought into optimum contact with the micro-organisms.

In accordance with a preferred embodiment, a filter is provided below the conic section of the tank and below the filter a removal station for the removal of the finished fermentation broth.

All components can be located in a stackable rack together with an automatic control. Such a stackable rack positioned on a pallet allows simple transportation and any combination of several fermenters through corresponding stacking.

Advantageously, a rotationally symmetrical vortex chamber is used as the atomising nozzle which chamber is formed by a jacket and two plates closing this at the ends with at least one inlet connection set tangentially to the jacket and at least one outlet opening provided on at least one plate. The vortex chamber of the atomising nozzle can also possess only one outlet opening and the plate provided with the outlet opening closing the jacket of the vortex chamber at the end side can simultaneously be the end plate of a pipe surrounding the vortex chamber. This pipe is then advantageously simultaneously the end of the lead leading from the circulating pump into the upper section of the tank.

The atomising nozzle per se is already known from WO 95/16521 of the same applicant.

Figure 2:
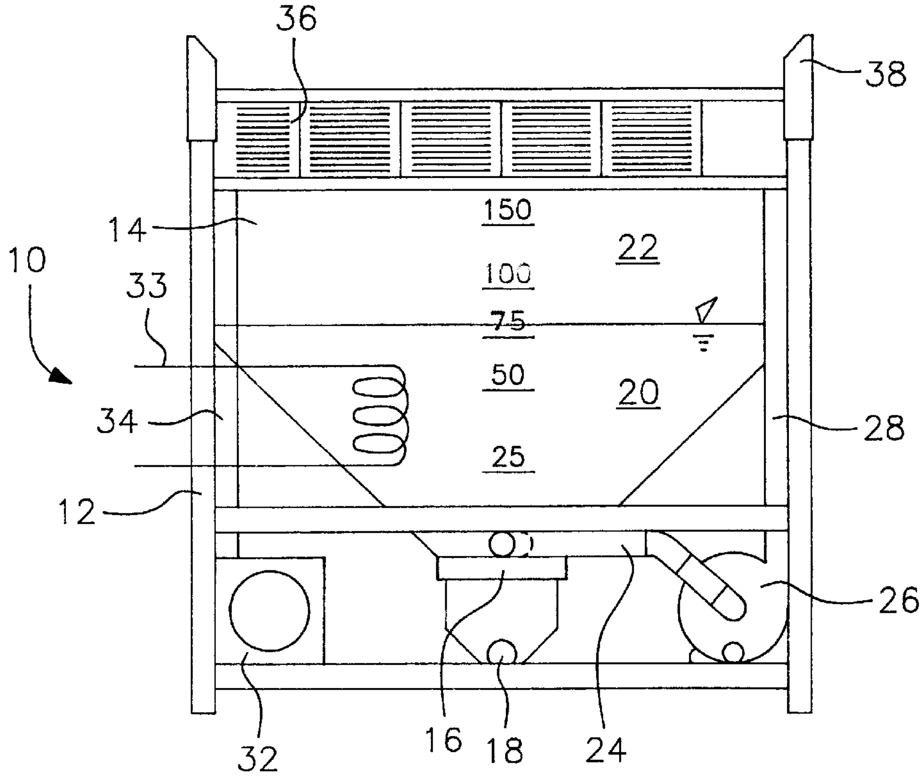
Figure 3:
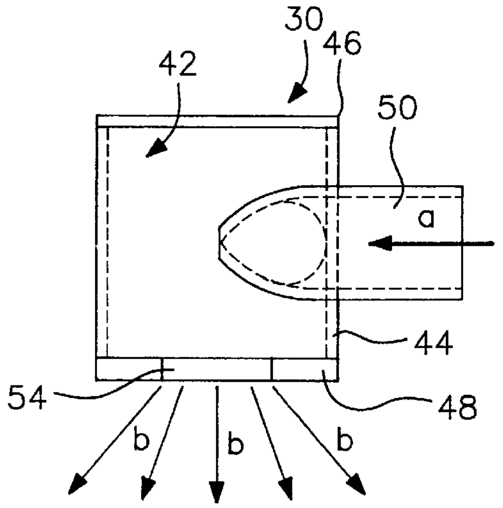
Figure 5:
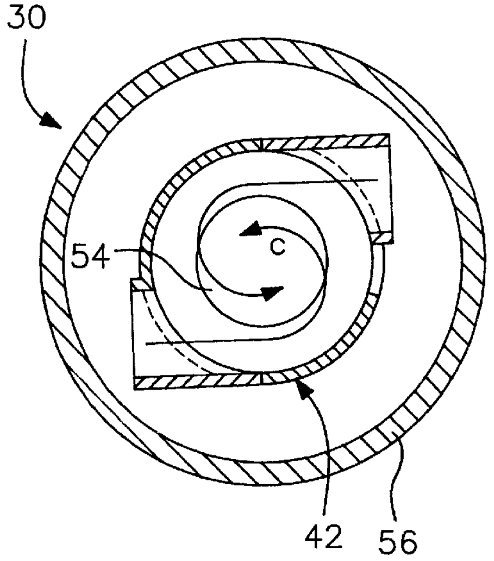
Figure 4:
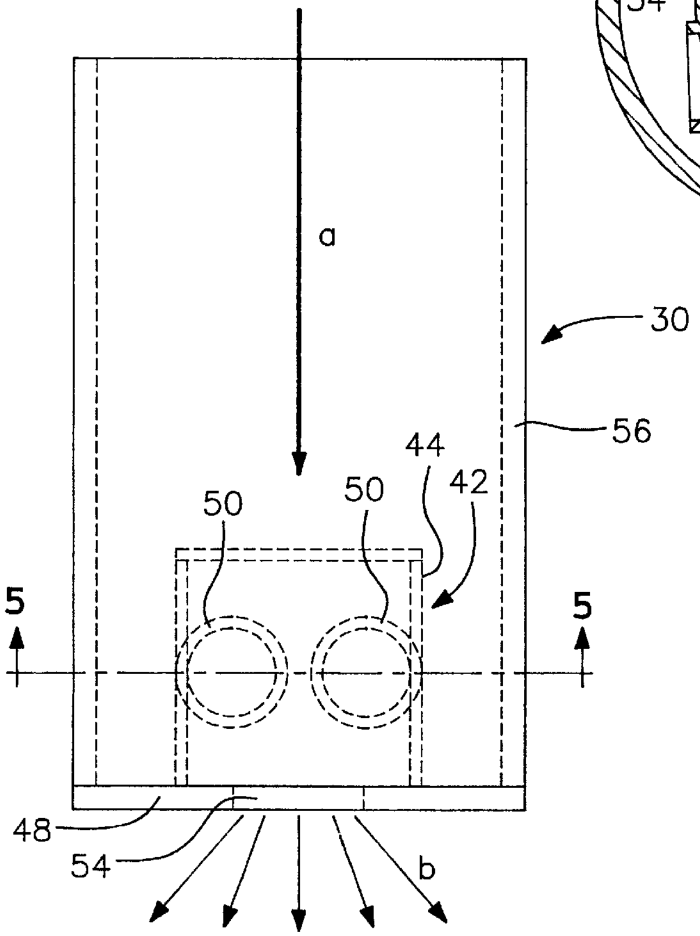

Further details and advantages of the invention are explained in detail by means of an embodiment presented in the drawing in which FIG. 1: is a top view of an embodiment of the apparatus in accordance with the invention;

FIG. 2: a side view of the embodiment in accordance with FIG. 1,

FIG. 3: a first embodiment of an atomising nozzle in accordance with the invention in a side view, and FIGS. 4 & 5: a second embodiment of the atomising nozzle in accordance with the invention.

The apparatus for the multiplication of micro-organisms, in brief also called the fermenter 10, is in accordance with the embodiment in FIGS. 1 and 2 integrated in a stackable rack 12. The fermenter 10 essentially comprises a tank 14 which is made, for example, from stainless steel and which possesses an upper cylindrical area and a lower conically shaped area extending to the bottom as shown in FIG. 2. Below the conical portion a filter 16 is provided. Below the filter is connected another cylindrical portion and a conically shaped portion with a removal opening 18 being provided for the finished product in the area of the conically shaped portion. The tank 14 is filled in its lower portion with fermentation broth 20. Process gas 22 is located above the surface of the fermentation broth in the tank 14. A lead 24, which leads to a circulating pump 26, issues into the lower area of the conically shaped section of the tank 14. A lead 28, at whose end an atomising nozzle 30 is provided, goes out of the circulating pump 26. This atomising nozzle 30 issues into the area of the tank 14 filled with process gas 22. To fill this area of the tank 14 with process gas 22, a device 32 is provided for the supply of process gas through a lead 34 into the area of the tank 14 filled with process gas. To perform aerobic fermentation, the device 32 will as a rule comprise a conventional aerator with an integrated air filter (not shown here). Alternatively, oxygen can also be supplied in aerobic fermentation. Other process gases for fermentation are, for example, $H_2O_2$ or ozone.

A control 36 with an operating panel and display instruments is also integrated in the rack 12. The rack 12 possesses stacking profiles 38 at its four corner areas. These stacking profiles 38 facilitate a simple and stable stacking of several racks 12 on top of each other.

In FIG. 3 an embodiment of an atomising nozzle 30 is shown. This comprises a rotationally symmetrical double chamber 42 possessing a jacket 44 with a circular cross-section. The jacket 44 possesses plates 46 and 48 which close it at the ends. The distance separating the end plates 46 and 46 represents the height of the chamber 42. As shown in FIG. 3, an inlet connection 50, the diameter of which is approximately one-half the height of the chamber 42, is fitted tangentially to the jacket 44, which connection can simultaneously be connected to the end area of the lead 28 in the gas area of the tank 14. The fermentation broth is led through the inlet connection 50 in the direction of the arrow a into the rotationally symmetrical vortex chamber. The fluid set in rotation there then exits from the outlet opening 54 in the direction of the arrows b exiting the outlet opening, the fluid is finely atomised by the centrifugal forces exerted on the fluid particles and thus mixed intensively with the surrounding process gas atmosphere.

A modified embodiment of the atomising apparatus 30 is shown in FIGS. 4 and 5. Here, the rotationally symmetrical vortex chamber 42, which essentially corresponds to the design in accordance with the embodiment in accordance with FIG. 1, but possessing two inlet connections 50 fitted tangentially offset with respect to one another to the jacket 44, is surrounded by a pipe lead 56 which represents the endpiece of the lead 28 in accordance with FIGS. 1 and 2. The plate 48 closing the jacket 44 of the vortex chamber 42 at the end simultaneously closes one end of the pipe lead 56 as is shown in FIG. 4. In FIG. 5 a section is shown through the atomising nozzle 30 along the line of intersection A—A.

The current flow of the fermentation broth to be atomised is made clear from the superimposition of FIGS. 4 and 5. The fermentation broth is supplied by the pump 26 and the lead 28 in the direction of the arrow a to the end area of the pipe lead referenced here as 56 and enters through the inlet connection 50 into the rotationally symmetrical vortex chamber 42. There, the fermentation broth is set into rotation in the direction of the arrow c (FIG. 5) before exiting from the outlet opening 54 and then being atomised in the direction of the arrows b.

In the fermentation tank 14 a conventional heat exchanger well known in the art is schematically illustrated by reference numeral 33 in FIG. 2. This heat exchanger can, for example, comprise heat exchanging coils contained in the tank 14. The heat exchanger is designed in such a way that it can, for example, supply heat at the start of fermentation. During fermentation itself, in which heat is produced, cooling must, however, be performed by means of the heat exchanger.

With the apparatus in accordance with the invention fermentation can, for example, be performed as follows. Fermentation is started by filling water into tank 14, adding a nutrient broth and then adding the inoculum, ie fresh compost, soil rich in microbes or industrially cultivated aerobic micro-organisms. Then, the desired temperature is set using the operating panel of the control 36 and the aeration of the nutrient solution is started through the device 32 for the supply of the process gas. In aerobic fermentation, the micro-organisms begin to multiply due to the oxygen enrichment and the nutrient solution and the process temperature rises. After some time, the optimum process temperature is reached and the fermentation broth is cooled using the heat exchanger.

The fermentation broth is circulated at regular intervals by the circulating pump 26 and thus finely atomised in the atomising nozzle 30 and mixed with the surrounding air and thus with the air oxygen. The atomised fermentation broth mixed with air is then collected in the lower section of the tank. The fermentation broth is circulated so frequently by the circulating pump 26 that due to the very fine atomisation and the mixing in of air, a very homogeneous distribution of the oxygen of the nutrient solution is achieved. By means of the apparatus in accordance with the invention, it is now ensured that the same favourable growth conditions prevail for the micro-organisms in all areas of the tank. This allows optimum process management of aerobic fermentation.

With the apparatus in accordance with the invention, it is possible to make available the optimum temperature and nutrient solution as well as the parameter oxygen for the fermentation. In this way, the micro-organisms multiply so fast that due to the metabolism the temperature rises very much. Micro-organisms which cannot stand high temperatures might be destroyed by this again. However, micro-organisms which withstand high temperatures could be further multiplied here. But for certain applications micro-organisms are required which grow in a certain temperature interval. The setting to such a desired temperature interval and thus to a certain micro-organism which grows in this temperature interval is possible by means of the heat exchanger. The heat extracted from the system can advantageously be made available in its place, for example, as heating warmth.

The fermentation is performed until the nutrient solution is consumed, which is indicated by a fall in temperature and which can be determined by the automatic control. On the fall in temperature below a certain limit value, the process gas supply is stopped and the cooling ceased. The finished fermentation broth can then be pumped out through the removal opening 18.

What is claimed is:

1. An apparatus for the multiplication of micro-organisms comprising a tank for holding a fermentation broth in its lower section, said fermentation broth maintained at a desired process temperature, a pump for the circulation of said fermentation broth, a heat exchanger for setting said desired process temperature, an inlet which supplies a process gas directly into the space in said tank above said fermentation broth, and at least one atomizing nozzle for atomization of the fermentation broth and mixing with said process gas, said atomizing nozzle positioned in said tank space above said fermentation broth and having a rotationally symmetrical vortex chamber which is formed by a jacket having two ends closed by two plates, at least one inlet connection fitted tangentially to the jacket and one outlet opening provided in one of the two plates, wherein said fermentation broth delivered to said at least one tangentially fitted inlet connection by said pump is mixed with said process gas via circular rotation in said symmetrical vortex chamber and out said outlet.

2. The apparatus according to claim 1, wherein the tank has a bottom and is conically shaped in a section extending to the bottom of the tank so as to form a cone, a first lead, which leads to the circulating pump, is connected at a lower region of the cone, at least one second lead, which extends from the circulating pump into an upper section of the tank, has an end which is fitted to the at least one atomizing nozzle.

3. The apparatus according to claim 2, further comprising a filter positioned below the conically shaped section of the tank and a removal station positioned below the filter for the removal of the fermentation broth.

4. The apparatus according to claim 3 further comprising an automatic control device.

5. The apparatus according to claim 4, further comprising a stackable rack.

6. The apparatus according to claim 1, further comprising two inlet connectors each having central lines, said connectors fitted tangentially to the jacket of the vortex chamber so that the central lines of the connectors run parallel and extend perpendicular to, and are spaced apart from, the axis of the jacket of the vortex chamber.

7. The apparatus of claim 1, further comprising a first lead extending from a bottom section of the tank to the circulating pump and at least one second lead extending from the circulating pump to an upper section of the tank and having an end region, said pipe being the end region of the at least one second lead.

8. The apparatus of claim 1, wherein said symmetrical vortex chamber and jacket are symmetrical and positioned in a pipe having an end plate which also serves as the end plate of said jacket provided with the outlet opening.

9. An apparatus for the multiplication of micro-organisms comprising a tank for holding a fermentation broth in a lower section of the tank, said fermentation broth maintained at a desired process temperature, at least one supply means for supplying a process gas to an upper section of the tank, and a pump for circulating the fermentation broth from adjacent the bottom of the tank to at least one atomizing nozzle positioned in said tank upper section, said at least one atomizing nozzle atomizing said fermentation broth and mixing said process gas such that the atomized fermentation broth is directly mixed with the process gas, said fermentation broth being in a quiescent state in the lower section of said tank without agitation.

10. The apparatus according to claim 9, further comprising said tank having a bottom which is conically shaped so as to form a cone, a first lead which leads to the circulating pump which is positioned outside said tank and is connected at a lower region of the cone, and at least one second lead which extends from the circulating pump into the upper section of the tank having an end which is fitted to the at least one atomizing nozzle.

11. The apparatus according to claim 10, further comprising a filter positioned below the conically shaped section of the tank and a removal station provided below the filter for the removal of the fermentation broth.

12. The apparatus according to claim 9, wherein said atomizing nozzle has a rotational symmetrical vortex chamber which is formed by a jacket having two ends each closed by a plate and at least one inlet connection fitted tangentially to the jacket.

13. The apparatus according to claim 12, further comprising said vortex chamber possessing only one outlet opening and being positioned in a pipe having an end plate which also serves as the end plate of the jacket provided with the outlet opening.

14. The apparatus according to claim 13, further comprising two inlet connectors each having central lines and being fitted tangentially to the jacket of the vortex chamber so that the central lines of the connectors run parallel and extend perpendicular to, and are spaced apart from, the axis of the jacket of the vortex chamber.

15. The apparatus according to claim 9, further comprising both plates of the jacket being arranged parallel to each other; one plate being closed and the other plate being provided with the at least one outlet opening through which said atomized fermentation broth exits.

* * * * *